(12) United States Patent
Clawson et al.

(10) Patent No.: US 7,402,561 B2
(45) Date of Patent: Jul. 22, 2008

(54) COMPOSITIONS AND METHODS FOR INHIBITING ABNORMAL CELL GROWTH

(75) Inventors: Gary Clawson, Bethesda, MD (US);
Craig Meyers, Hummelstown, PA (US);
David Drubin, Jamaica Plain, MA (US);
Molly McLaughlin-Drubin, Jamaica Plain, MA (US)

(73) Assignee: Clawnor, Inc., Bethesda, MD (US)

( * ) Notice: Subject to any disclaimer, the term of this patent is extended or adjusted under 35 U.S.C. 154(b) by 0 days.

(21) Appl. No.: 11/076,680

(22) Filed: Mar. 9, 2005

(65) Prior Publication Data

US 2005/0209150 A1    Sep. 22, 2005

Related U.S. Application Data

(60) Provisional application No. 60/552,026, filed on Mar. 10, 2004.

(51) Int. Cl.
*A01N 37/18* (2006.01)
(52) U.S. Cl. ..................... 514/2; 530/300; 530/388.3; 435/213; 524/94.64; 514/934
(58) Field of Classification Search ................. None
See application file for complete search history.

(56) References Cited

U.S. PATENT DOCUMENTS

| 4,518,528 A | 5/1985 | Rasnick | ................ 260/112.5 R |
| 4,636,492 A | 1/1987 | Kettner et al. | ................. 514/18 |
| 6,358,928 B1 | 3/2002 | Rasnick | ....................... 514/17 |

OTHER PUBLICATIONS

Stoppler, et al., Oncogene, 1996, 13, 1545-1548.*
Voet, et al., Biochemistry, 1995, John Wiley & sons, Inc., p. 841.*
Rapp, et al., Biochimica et Biophysica Acta 1998, 1378, F1-F19.*
Oda, et al., Experimental Cell Research, 1996, 226, 164-169.*
"Nuclear Scaffold-Associated Protease: In Situ Nuclear Localization and Effects of a Protease Inhibitor on Growth and Morphology of a ras-Transformed Hepatocyte Cell Line," Gary A. Clawson, Ling Ren, and Harriet C. Isom, Hepatology, vol. 22, No. 4, 1995.
"The Mr 46,000 Nuclear Scaffold ATP-binding Protein: Identification of the Putative Nucleoside Triphosphatase by Proteolysis and Monoclonal Antibodies Directed Against Lamins A/C," Gary A. Clawson, Yan-Fei Wang, Arnold M. Schwartz, and Christine L. Hatem, Cell Growth and Differentiation, vol. 1, 559-568, Nov. 1990.
"Ca2+=regulated Serine Protease Associated with the Nuclear Scaffold," Gary A. Clawson, Lauri L. Norbeck, Christine L. Hatem, Cheryl Rhodes, Payman Amiri, James H. McKerrow, Steven R. Patierno, and Gary Fiskum, Cell Growth & Differentiation, vol. 3, 827-838, Nov. 1992.
"An Inhibitor of Nuclear Scaffold Protease Blocks Chemical Transformation of Fibroblasts," Gary A. Clawson, Lauri L. Norbeck, John P. Wise, and Steven R. Patierno, Cell Growth & Differentiation, vol. 4, 589-594, Jul. 1993.

"Proteolytic Activity Associated with the Nuclear Scaffold—The Effect of Self-Digestion on Lamins," Zoltan A. Tokes and Gary A. Clawson, J. Biol. Chem., vol. 264, No. 25, Sep. 5, 1989, pp. 15059-15065.
The serine protease inhibitors TLCK and TPCK inhibit the invitro immortalization of primary human keratinocytes by HPV-18 DNA, Hubert Stoppler, Debra Koval and Richard Schlegel, Oncogene (1996) 13, 1545-1548.
"The Serine Protease Inhibitors TLCK and TPCK React with the RB-Binding Core of HPV-18 E7 Protein and Abolish its RB-Binding Capability," Hubert Stoppler, Melissa Conrad Stoppler, Alexander Adduci, Debra Koval, and Richard Schlegel, Virology 217, 542-553 (1996).
"Proline-Valine Pseudo Peptide Enol Lactones-Effective and Selective Inhibitors of Chymotrypsin and Human Leukocyte Elastase," Peter E. Reed and John A. Katzenellenbogen, J. Biol. Chem., vol. 266, No. 1, Issue of Jan. 5, 1991, pp. 13-21.
Itoh, Hiroshi, Hiroaki Kataoka, Masamichi Yamauchi, Seiji Naganuma, Yutaka Akiyama, Yoshitsugu Nuki, Takeshi Shimomura, Keiji Miyazawa, Naomi Kitamura, Masashi Koono, "Identification of Hepatocyte Growth Factor Activator Inhibitor Type 2 (HAI-2)-Related Small Peptide (H2RSP): Its Nuclear Localization and Generation of Chimeric mRNA Transcribed from both HAI-2 and H2RSP Genes," Biochemical and Biophysical Research Communications 288, 390-399 (2001).
Bury, M., Mlynarczuk, I., Pieban, E., Hoser, G., Kawiak, J., and Wojcik, C.; Effects of an inhibitor of tripeptidyl peptidase II (Ala-Ala-Phe-chloromethylketone) and its combination with an inhibitor of the chymotrypsin-like activity of the proteasome (PSI) on apoptosis, cell cycle and proteasome activity in U937 cells. 2001. Folia Histochimica et Cytobiologica 39:131-132.
Geier, E., Preifer, G., et al. A giant protease with potential to substitute for some functions of the proteasome. 1999. Science 283:978-981.
Osmulski, P., Gaczynska, M. A new large proteolytic complex distinct from the proteasome is present in the cytosol of fission yeast. 1998. Curr. Biol. 8:1023-1026.
Hori, H., Nembai, T., Miyata, Y., Hayashi, T., Ueno K., and Koide, T.; Isolation and characterization of two 20S proteasomes from the endoplasmic reticulum of rat liver microsomes. 1999. J. biochem (Tokyo) 126:722-730.
J. Powers, "Haloketone Inhibitors of Proteolytic Enzymes," in Chemistry and Biochemistry of Amino Acids, Peptides, and Proteins, B. Weinstein (ed.), vol. 4, Marcel-Dekker, NY, 1977, pp. 65-178.

* cited by examiner

*Primary Examiner*—Anish Gupta
*Assistant Examiner*—Satyanarayana R. Gudibande
(74) *Attorney, Agent, or Firm*—Gifford, Krass, Sprinkle, Anderson & Citkowski, PC

(57) ABSTRACT

In the US about ⅓ of college women show evidence of HPV infection. The clinical problem may be even larger in developing countries. There are currently no effective therapies for HPV infections, aside from therapeutic cone biopsies, which often are followed by recurrent, progressive lesions. Thus, pharmaceutical compositions and processes for treatment of an HPV infection are detailed. In particular, a pharmaceutical composition for inhibiting growth of a human papilloma virus-infected cell is provided which includes a peptide halomethyl ketone inhibitor of a chymotrypsin or chymotrypsin-like protease and a pharmaceutically acceptable carrier. A preferred inhibitor is AAPFcmk.

13 Claims, 4 Drawing Sheets

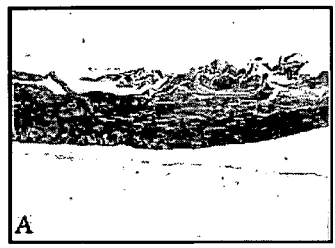
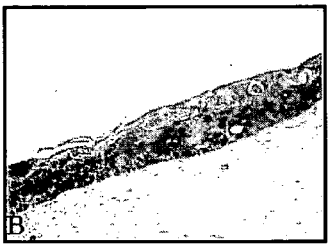
Figure 2A               Figure 2B
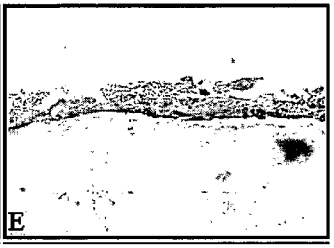
Figure 2C            Figure 2D            Figure 2E
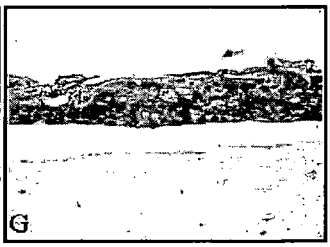
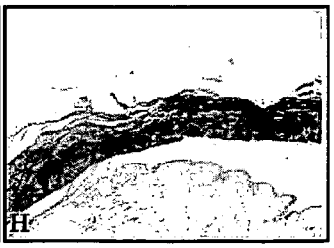
Figure 2F            Figure 2G            Figure 2H

COMPOSITIONS AND METHODS FOR INHIBITING ABNORMAL CELL GROWTH

REFERENCE TO RELATED APPLICATIONS

This application claims priority of U.S. Provisional Patent Application 60/552,026 filed Mar. 10, 2004, which is incorporated herein by reference in its entirety.

FIELD OF THE INVENTION

The invention relates to compositions and methods for inhibiting growth of virus infected cells In particular, the invention relates to compositions and methods for inhibiting growth of human papilloma virus (HPV) infected cells.

BACKGROUND OF THE INVENTION

Tumorigenesis is a complex process which has not been fully characterized to date. Mechanisms of tumorigenesis are the subject of intensive research since there is a continuing need for pharmaceuticals capable of interrupting a cascade of events leading to tumor formation. A number of causative events may trigger a tumorigenic cascade, including viral infection, spontaneous transformation, exposure to toxins among others.

Infection with Human Papllomaviruses (HPV) is believed to be one such causative event. Human Papllomaviruses are implicated in causation of nearly all cases of cervical cancer. Certain types of HPV are termed "high-risk", in that infection with them is associated with development of high-grade cervical dysplasias which may progress to carcinomas.

HPVs, a subset of the papillomaviruses, are members of the Papillomaviridae family of viruses (31). The HPVs are small, double stranded, circular DNA viruses with an icosahedral, non-enveloped virion of about 55 nm in diameter and a genome of 8 kb. HPVs infect human squamous epithelium and induce papillomas (or warts). While there are many types of HPV able to infect various anatomical regions, it is the HPVs that infect the anogenital region that have been the best studied. Among this group, HPVs can be divided based upon the frequency with which they induce malignancy. The low risk HPVs can cause benign warts, but are rarely observed in malignant cancers. This group is represented by HPV types 6, 11, 42, 43, and 44. HPV types 16, 18, 31, 33, 39, 45, and 56 constitute the high risk HPVs, which are most often associated with malignant cervical cancers (2).

HPV is the prime etiological factor in the development of cervical cancer, being associated with over 90% of all cases (32). In addition to this epidemiological statistic, the IARC ultimately declared HPV 16 and 18 carcinogenic in humans (33) based upon a number of pieces of evidence including in vitro immortalization differences between high risk and low risk viruses (high risk HPVs can immortalize keratinocytes and low risk HPVs cannot (34) and the presence of active viral genomes and oncoproteins in cells of the tumor and associated metastases (35, 36, 37, 38).

Estimates vary, but in the US about ⅓ of college women show evidence of HPV infection. HPV infection typically manifests itself as cervical intraepithelial dysplasia (CIN) of three types, mild dysplasia or CIN1, moderate dysplasia or CIN2 and severe dysplasia or cervical carcinoma, referred to as CIN3. The mean age for CIN1 and CIN2 is 24-27 years, and for CIN3 is it 35-42 years. About 50% of CIN1 cases regress, whereas about 10% progress to CIN 3 and 2% progress to cervical cancer. While NIH-funded vaccine development shows promise, there are millions of patients who will develop CIN3 over the next 10 years, and who will require lifelong (>50 years) monitoring and treatment. The clinical problem may be even larger in developing countries. There are currently no effective therapies for HPV infections, aside from therapeutic cone biopsies, which often are followed by recurrent, progressive lesions.

Thus, there exists a need for compositions and methods for treating HPV infected cells and particularly for inhibiting growth of HPV-infected cells.

SUMMARY OF THE INVENTION

A pharmaceutical composition for inhibiting growth of a human papilloma virus-infected cell is provided which includes a peptide halomethyl ketone inhibitor of a chymotrypsin or chymotrypsin-like protease and a pharmaceutically acceptable carrier.

In one embodiment, the inhibitor includes the structure $(X)_nY$—R, where $(X)_nY$ is a peptide, where n is an integer in the range of 0-10, inclusive, where each X is an amino acid residue of an amino acid independently selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, phenylglycine, norleucine, norvaline, alpha-aminobutyric acid, citrulline, hydroxyproline, ornithine, and homoarginine; Y is selected from the group consisting of: tryptophanyl, tyrosinyl, phenylalaninyl, methioninyl and leucinyl; and where R is a halomethyl moiety. Optionally more than one inhibitor in included in an inventive composition.

Optionally and preferably an inhibitor includes an N-terminal protecting group, Z, such that the inhibitor comprises the structure Z-$(X)_nY$—R.

In a preferred option, the inhibitor includes a moiety $(X)_nY$, wherein $(X)_nY$ is alaninyl-alaninyl-prolinyl-phenylalaninyl. Also preferred is an inhibitor wherein $(X)_nY$ is selected from the group consisting of: valinyl-prolinyl-phenylalaninyl and leucinyl-leucinyl-phenylalaninyl.

Particularly preferred is an embodiment in which R is a chloromethyl moiety. Also particularly preferred is an embodiment in which an inhibitor included in the composition is AAPF chloromethyl ketone.

In a further embodiment, a provided composition described herein includes an selected from the group consisting of: VPF chloromethyl ketone, LLF chloromethyl ketone, AAF chloromethyl ketone, LLVY chloromethyl ketone, GGL chloromethyl ketone, AAPY chloromethyl ketone and LY chloromethyl ketone and combinations thereof.

Optionally, an included inhibitor includes a targeting moiety for targeting the inhibitor to a subcellular location, preferably a nuclear localization signal.

In a further embodiment, the inhibitor includes the structure N—S—$(X)_nY$—R, wherein $(X)_nY$ is a peptide, where n is an integer in the range of 0-10, inclusive, where each X is an amino acid independently selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, phenylglycine, norleucine, norvaline, alpha-aminobutyric acid, citrulline, hydroxyproline, ornithine, and homoarginine.; Y is selected from the group consisting of: tryptophanyl, tyrosinyl, phenylalaninyl, methioninyl and leucinyl; where R is a halomethyl moiety and where N is a nuclear localization signal and where S is a spacer amino acid residue or peptide. Optionally, an N-terminal protecting group, Z is included such that the inhibitor has the formula Z-N—S—(X)$_n$Y—R.

In one embodiment, a provided composition includes an inhibitor having a nuclear localization signal with the formula KKXK-(G)$_n$, where X is an amino acid residue, and n is an integer in the range from 1-20, inclusive.

Also detailed herein is a provided composition wherein the inhibitor includes the structure $(X_1)_{n1}(X_2)_{n2}Y$—R, where $(X_1)_{n1}(X_2)_{n2}Y$ is a peptide, where n1 and n2 are each independently an integer in the range of 0-4, inclusive, where each $X_1$ is an independently selected hydrophobic amino acid residue; where each $X_2$ is a residue of an amino acid independently selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, phenylglycine, norleucine, norvaline, alpha-aminobutyric acid, citrulline, hydroxyproline, ornithine, and homoarginine; Y is selected from the group consisting of: tryptophanyl, tyrosinyl, phenylalaninyl, methioninyl and leucinyl; and where R is a halomethyl moiety. Z is an optional N-terminal protecting group such that the structure of the inhibitor includes Z-$(X_1)_{n1}(X_2)_{n2}$Y—R. A hydrophobic amino acid is selected from the group consisting of: alanine, cysteine, glycine, isoleucine, leucine, proline, serine, threonine, and valine. In one embodiment, n1 is 2 and n2 is 1. Optionally, each of the two X1 amino acids is identical, such as AA, GG and the like. Particularly preferred is the AA motif.

In a particularly preferred option, a provided composition is formulated for topical administration.

Also provided is a process of inhibiting a viral infection which includes a step of providing a composition as described herein; and contacting a cell infected with a human papilloma virus with an amount of the composition effective to inhibit growth of the cell, such that a viral infection is inhibited. Preferably such a process is applied where the human papilloma virus is a strain of human papilloma virus associated with a predisposition to transform an infected cell. Such a human papilloma viruses are HPV16, HPV18, HPV31, HPV33, HPV39, HPV45, and HPV56.

Further provided is a process of treating a subject infected with a strain of human papilloma virus, including the steps of providing a composition as described herein and administering a therapeutically effective amount of the composition to the subject. In general the subject is a human. Preferably such a process is applied where the human papilloma virus is a strain of human papilloma virus associated with a predisposition to transform an infected cell. Such a human papilloma viruses are HPV16, HPV18, HPV31, HPV33, HPV39, HPV45, and HPV56. Further preferably the step of administering a composition includes topical administration of the composition. Topical administration is preferably to an area affected by the virus, such as genital, anal and cervical tissues.

Further described is an inventive process of inhibiting a viral infection which includes the steps of providing a composition as detailed herein and contacting a cell infected with a human papilloma virus with an amount of the composition effective to decrease viral DNA in the cell, such that a viral infection is inhibited. Preferably such a process is applied where the human papilloma virus is a strain of human papilloma virus associated with a predisposition to transform an infected cell. Such a human papilloma viruses are HPV16, HPV18, HPV31, HPV33, HPV39, HPV45, and HPV56.

In a preferred embodiment a process of inhibiting a viral infection is provided which includes providing a composition described herein and contacting a plurality of cells with a therapeutic amount of the composition, the plurality of cells comprising a first population of cells infected with a human papilloma virus and a second population of cells uninfected by the human papilloma, the therapeutic amount of the composition effective to selectively inhibit growth of the first population of cells and non-toxic to the second population of cell, such that a viral infection is inhibited.

In a preferred embodiment a process of inhibiting a viral infection is provided which includes providing a composition described herein and contacting a plurality of cells with a therapeutic amount of the composition, the plurality of cells comprising a first population of cells infected with a human papilloma virus and a second population of cells uninfected by the human papilloma, the therapeutic amount of the composition effective to decrease viral DNA in the plurality of cells and non-toxic to the second population of cell, such that a viral infection is inhibited.

BRIEF DESCRIPTION OF THE DRAWINGS

FIG. 2A is a digital image of untreated HPV31b infected CIN-612 9E cells grown in organotypic raft culture;

FIG. 2B is a digital image of HPV31b infected CIN-612 9E cells grown in organotypic raft culture treated with 0.25% DMSO solvent control;

FIG. 2C is a digital image of HPV31b infected CIN-612 9E cells grown in organotypic raft culture treated with 10 micromolar AAPFcmk;

FIG. 2D is a digital image of HPV31b infected CIN-612 9E cells grown in organotypic raft culture treated with 25 micromolar AAPFcmk;

FIG. 2E is a digital image of HPV31b infected CIN-612 9E cells grown in organotypic raft culture treated with 50 micromolar AAPFcmk;

FIG. 2F is a digital image of HPV31b infected CIN-612 9E cells grown in organotypic raft culture treated with 10 micromolar GRcmk;

FIG. 2G is a digital image of HPV31b infected CIN-612 9E cells grown in organotypic raft culture treated with 25 micromolar GRcmk;

FIG. 2H is a digital image of HPV31b infected CIN-612 9E cells grown in organotypic raft culture treated with 50 micromolar GRcmk;

DETAILED DESCRIPTION OF THE INVENTION

Figure 1:
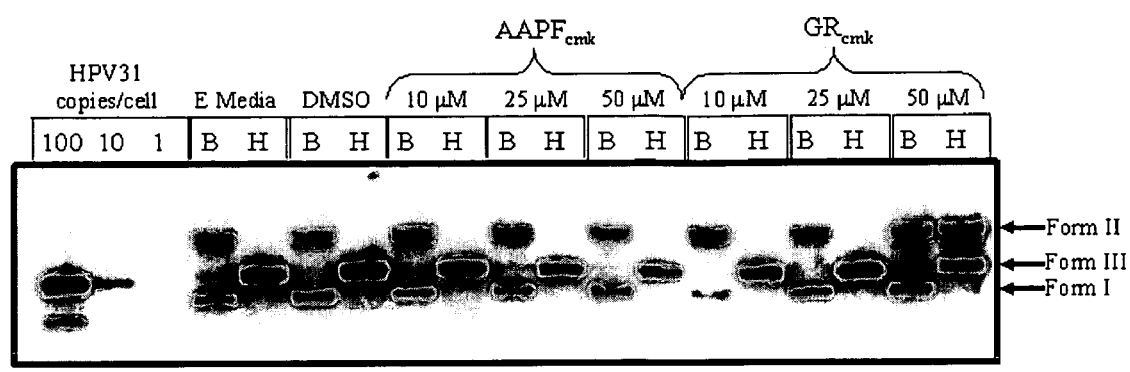
FIG. 1 is a digital image of a Southern illustrating reduction of HPV DNA content in cells treated with an inventive composition.

Cervical cancer is the most common cancer in developing countries and the second most common cancer in women worldwide (1). Essentially all cervical cancers are thought to involve human papillomavirus (HPV) infections (2, 3), such that compositions and processes for treatment of such infections are needed. The present invention provides pharmaceutical compositions and processes for treatment and inhibition of HPV infection, along with processes for inhibition of growth of cells infected with HPV.

In particular, a pharmaceutical composition is provided for inhibiting growth of a human papilloma virus-infected cell. In one embodiment of the invention an inventive composition includes a peptide halomethyl ketone inhibitor of a chymotrypsin or chymotrypsin-like protease and a pharmaceutically acceptable carrier.

Inhibitor

In one embodiment, a peptide halomethyl ketone inhibitor of a chymotrypsin or chymotrypsin-like protease generally has the structure Z-$(X)_n$Y—R. The moiety $(X)_n$Y is a peptide or amino acid such that n is an integer in the range of 0-10, inclusive and each X is a residue of an amino acid independently selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, phenylglycine, norleucine, norvaline, alpha-aminobutyric acid, citrulline, hydroxyproline, omithine, and homoarginine.

Chymotrypsin and chymotrypsin-like enzymes hydrolyze peptide bonds where the carboxyl amino acid at the cleavage site is Trp, Tyr, Phe, Met, Leu or other amino acid residues which contain aromatic or large alkyl side chains. Thus, Y is an amino acid residue preferably selected from the group consisting of: tryptophanyl, tyrosinyl, phenylalaninyl, methioninyl and leucinyl.

Z is an N-terminal protecting group. The particular choice of the N-terminal protecting group used in the inhibitor depends on various factors, such as the effect of the group on enzyme specificity, inhibitor solubility, and convenience. Suitable protecting groups are known in the art and an appropriate group will be recognized by one of skill in the art. Such protecting groups illustratively include carbobenzyloxy, benzoyl, t-butyloxycarbonyl, glutaryl, p-tolylsulfonyl, methoxysuccinyl, and succinyl groups.

In a preferred embodiment, R is a halomethyl moiety, such as a fluoromethyl, chloromethyl or bromomethyl group. Particularly preferred is an embodiment in which R is chloromethyl.

The terms "amino acid" and "amino acid residue" are known in the art. In general the abbreviations used herein for designating the amino acids and protective groups conform to those used by the IUPAC-IUB Commission on Biochemical Nomenclature, see for example Biochemistry (1972) 11:1726-1732. The following abbreviations are used in the present specification in referring to specific amino acids and/or amino acid residues: A or Ala for alanine, C or Cys for cysteine, D or Asp for aspartic acid, E or Glu for glutamic acid, F or Phe for phenylalanine, G or Gly for glycine, H or His for histidine, I or Ile for isoleucine, K or Lys for lysine, L or Leu for leucine, M or Met for methionine, N or Asn for asparagine, P or Pro for proline, Q or Gln for glutamine, R or Arg for arginine, S or Ser for serine, T or Thr for threonine, V or Val for valine, W or Trp for tryptophan, and Y or Tyr for tyrosine.

When the carboxyl carbon atom of one amino acid covalently binds to the amino nitrogen atom of another amino acid with the release of a water molecule, a peptide bond is formed. The portion of the amino acid which remains after losing a water molecule when it is joined to another amino acid is generally termed an amino acid residue. Amino-acid residues are therefore structures that lack a hydrogen atom of the amino group (—NH—CHR—COOH), or the hydroxyl moiety of the carboxyl group (NH2—CHR—CO—), or both (—NH—CHR—CO—); all units of a peptide chain are therefore amino-acid residues.

The acyl group of an -amino-mono-carboxylic acid is a structure that lacks the hydroxyl group of the carboxyl (H2N—CHR—CO—). The names of such groups are formed by replacing the ending 'ine' (or 'an' in tryptophan) by 'yl', e.g. alanyl, arginyl, tryptophyl.

The monoacyl groups derived from aspartic acid, HOOC—CH2—CH(NH2)—CO— and —CO—CH2—CH(NH2)—COOH, are designated -aspartyl (or aspart-1-yl) and -aspartyl (or aspart-4-yl) respectively; the corresponding groups derived from glutamic acid are -glutamyl (or glutam-1-yl) and -glutamyl (or glutam-5-yl). The diacyl groups formed from the dicarboxylic amino acids are aspartoyl and glutamoyl. The acyl groups derived from asparagine and glutamine are termed asparaginyl and glutaminyl respectively.

To name peptides, the names of acyl groups ending in 'yl' are used. Thus if the amino acids glycine, NH3+-CH2—COO—, and alanine, NH3+—CH(CH3)—COO—, condense so that glycine acylates alanine, the dipeptide formed, NH3+—CH2—CO—NH—CH(CH3)—COO—, is named glycylalanine. If they condense in the reverse order, the product, NH3+—CH(CH3)—CO—NH—CH2—COO—, is named alanylglycine. Higher peptides are named similarly, e.g. alanylleucyltryptophan. Thus the name of the peptide begins with the name of the acyl group representing the N-terminal residue, and this is followed in order by the names of the acyl groups representing the internal residues. Only the C-terminal residue is represented by the name of the amino acid, and this ends the name of the peptide.

If the hydroxyl group of the 1-carboxyl is replaced by an alkyl group, the name of the ketone formed can use the name of the amino acid by naming the compound as a substituted hydrocarbon, e.g. phenylalanylchloromethane for C6H5—CH2—CH(NH2)CO—CH2Cl, 3-amino-1-chloro-4-phenylbutan-2-one. This type of name is based on the trivial names of amino acids (or peptides), so does not place the substituents of methane in alphabetical order (as systematic nomenclature does), but places 'chloromethane' at the end because this indicates C-terminal modification. While practice of using names such as 'phenylalanine chloromethyl ketone' is discouraged, because they erroneously specify the carbonyl group twice, the term is commonly and interchangeably used to designate phenylalanylchloromethane. Thus, a peptide chloromethyl ketone included in an inventive composition is commonly referred to by designating the amino acid residues by the common amino acid abbreviations, followed by cmk to indicate chloromethyl ketone. For example, AAPFcmk indicates alanylalanylprolinylphenylalanyl chloromethyl ketone which, according to IUPAC nomenclature may also be designated alanylalanylprolinylphenylalanylchloromethane. Thus, in the structural formula described for an inhibitor included in an inventive composition $(X)_nY$—R, each amino acid residue X and Y may be referred to by the common amino acid abbreviation or name to indicate the amino acid residues included.

The term "amino acid residue" optionally further includes analogs, derivatives and congeners of any specific amino acid referred to herein, as well as C-terminal or N-terminal protected amino acid derivatives. For example, an amino acid analog may be used wherein a side chain is modified while still providing a carboxyl, amino or other reactive functional group. For example, amino acid analogs illustratively include canavanine, cyanoalanine, diaminobutyric acid, diaminopimelic acid, dihydroxy-phenylalanine norleucine, 3-phosphoserine, homoserine, 5-hydroxytryptophan, 1-methylhistidine, 3-methylhistidine, and ornithine.

Examples of chymotrypsin and chymotrypsin-like protease inhibitors which are peptide halomethyl ketones included in an inventive composition are illustrated in standard references such as Powers, J. C., 1977, "Haloketone Inhibitors of Proteolytic Enzymes", in Weinstein,B. (ed.), "Chemistry and Biochemistry of Amino Acids, Peptides and Proteins.", Marcel Decker, New York, pp. 65-178. The reference describes various haloketone derivatives of amino acids and peptides which inhibit proteases and is incorporated herein by reference in its entirety.

An amino acid or peptide which is part of an inhibitor included in an embodiment of an inventive pharmaceutical composition may be described by the formula: $(X)_nY$ as described above. In one embodiment, preferred inhibitors include those having the $(X)_nY$ moiety alaninyl-alaninyl-prolinyl-phenylalaninyl. In another embodiment, further preferred inhibitors include those having the $(X)_nY$ moiety valinyl-prolinyl-phenylalaninyl and leucinyl-leucinyl-phenylalaninyl.

In one embodiment of an inventive pharmaceutical the inhibitor includes the structure $Z-(X_1)_{n1}(X_2)_{n2}Y$—R. In such an embodiment, $(X_1)_{n1}(X_2)_{n2}Y$ is a peptide and n1 and n2 are each independently an integer in the range of 0-4, inclusive. Further, each $X_1$ is an independently selected hydrophobic amino acid. Hydrophobic amino acids illustratively include alanine, cysteine, glycine, isoleucine, leucine, proline, serine, threonine, and valine. Further each $X_2$ in such an embodiment is an amino acid independently selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, phenylglycine, norleucine, norvaline, alpha-aminobutyric acid, citrulline, hydroxyproline, ornithine, and homoarginine. In addition, Y is an amino acid selected from the group consisting of: tryptophanyl, tyrosinyl, phenylalaninyl, methioninyl and leucinyl and R is a halomethyl moiety, such as fluoromethyl and preferably chloromethyl. Z is included in a preferred option and is an N-terminal protecting group.

In a preferred embodiment n1 is 2 and n2 is 1 such that the inhibitor comprises the structure $(X_1)_2(X_2)Y$. Also preferred is an embodiment in which the inhibitor comprises the structure $(X_1)_2(X_2)Y$. and the two $X_1$ amino acids are identical. Further preferred is an embodiment in which the inhibitor comprises the structure $(X_1)_2(X_2)Y$ and the two $X_1$ amino acids are glycine.

A highly preferred embodiment, peptide halomethyl ketone is AAPF-chloromethyl ketone. This inhibitor is described in such references as Clawson G A, et al., Hepatology., 1995 22(4 Pt 1):1230-5. and Pereira P J, et al. J Mol Biol., 1999 286(1):163-73. A commercial preparation of the inhibitor AAPF-chloromethyl ketone is available from Enzyme System Products, Livermore, Calif.

In a further embodiment, other preferred inhibitors included in an inventive pharmaceutical composition are VPF chloromethyl ketone, LLF chloromethyl ketone, AAF chloromethyl ketone, LLVY chloromethyl ketone, GGL chloromethyl ketone, and LY chloromethyl ketone.

In another embodiment, the inhibitor optionally includes a targeting moiety for targeting the inhibitor to a subcellular location. Targeting moieties are known in the art and include peptides directing localization of a substance to a particular subcellular compartment, such as the endoplasmic reticulum or nucleus.

In a highly preferred embodiment, the targeting moiety is a nuclear localization signal. In one embodiment a protease target of an inhibitor included in an inventive composition is localized to the inner nuclear envelope of a cell infected with a high risk strain of a human papilloma virus. Thus, delivery of an inhibitor to the nucleus of such a cell is desirable. For example, in one embodiment, the inhibitor includes the structure $Z-N-(X)_nY$—R, where Z, n, X, Y and R are as described herein and where N is a nuclear localization signal. In a further embodiment, a spacer S, is interposed between the nuclear localization signal and the amino acid or peptide $(X)_nY$. Exemplary nuclear localization sequences useful in an inventive composition are described in references including Dingwall, C., and Laskey, R. Nuclear targeting sequences—a consensus? 1991, Trends Biochem. Sci. 16:478-481; Gorlich, D., Kutay, U. Transport between the cell nucleus and the cytoplasm. 1999, Annu. Rev. Cell Dev. Biol. 15:607-660; Mattaj, I., Englmeier. Nucleocytoplasmic transport: the soluble phase. 1998, Annu. Rev. Biochem 67:265-306; Nakielny, S., Dreyfuss, G. Transport of proteins and RNAs in and out of the nucleus. 1999, Cell 99:677-690. An exemplary nuclear localization signal has the formula KKXK, where X is an amino acid. Also preferred is a nuclear localization signal and spacer having the formula $KKXK-(G)_n$, where $(G)_n$ is a spacer S, G is a glycine and n is an integer in the range from 1-20, inclusive.

An inhibitor included in an inventive pharmaceutical composition is produced by synthetic methods known in the art. For example, synthesis and formulation of a peptide component of an inhibitor is accomplished according to methods known in the art such as described for example in Pharmaceutical Formulation Development of Peptides and Proteins by Sven Frkjr, Lars Hovgaard, S°En Frokjaer, CRC Press (1999). Further, synthesis of halomethyl derivatives of peptides is also known in the art such as described in U.S. Pat. No. 4,518,528, for instance.

Pharmaceutically Acceptable Carrier

Depending on the intended mode of administration, the pharmaceutical composition can be in the form of solid, semisolid or liquid dosage forms, such as, for example, suppositories, powders, liquids, or suspensions.

As used herein, the term "pharmaceutically acceptable carrier" refers to a carrier medium which does not interfere with the effectiveness of the inhibitor and which is not toxic to the cell or subject at the concentrations at which it is administered.

For solid compositions, conventional nontoxic solid carriers include, for example, pharmaceutical grades of mannitol, lactose, starch, magnesium stearate, sodium saccharine, talc, cellulose, glucose, sucrose and magnesium carbonate.

Liquid pharmaceutically administrable compositions can, for example, be prepared by dissolving or dispersing an inhibitor in a carrier, such as water, saline, aqueous dextrose, glycerol, or ethanol, to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's Pharmaceutical Sciences by Joseph P. Remington, Mack Pub. Co., 1985 and A. Gennaro, Remington: The Science and Practice of Pharmacy, 2000, Lippincott, Williams & Wilkins.

A carrier suitable use in an inventive composition includes physiologically acceptable sterile aqueous or non-aqueous solutions, dispersions, suspensions or emulsions, and sterile powders for reconstitution into sterile administrable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like.

Liquid dosage forms include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectables can be prepared in conventional forms, either liquid solutions or suspensions, solid forms suitable for solution or prior to injection, or as suspension in liquid prior to injection or as emulsions.

Optionally, a pharmaceutical composition includes further medicinal agents, pharmaceutical agents, carriers, or diluents.

In one embodiment, an inventive composition is formulated in unit dosage form suitable for single administration of a precise dosage. In further embodiments, a composition is formulated in unit dosage form suitable for delivery of multiple doses delivered at specified intervals. Time release preparations are specifically contemplated as effective dosage formulations. The compositions will include an effective amount of the selected inhibitor in combination with a pharmaceutically acceptable carrier.

In a preferred embodiment, an inventive composition is formulated for topical administration. A topical formulation, broadly described, optionally include carrier components such as diluting or solubilizing agents for diluting or solubilizing an inhibitor, thickeners, gel formers, film-forming ingredients, and encapsulating agents for inhibiting evaporation or an inhibitor or dilution by fluids such as bodily fluids or exogenously applied fluids, emulsifiers, and antimicrobial agents for inhibiting contaminants.

Exemplary carriers for topical formulations of an inventive composition are described in the examples.

In one embodiment, a cyclodextrin is included in an inventive composition and may provide a protective coating or microencapsulation to an inhibitor in a composition. Cyclodextrins illustratively include beta.-cyclodextrin and gamma.-cyclodextrin. A particular cyclodextrin is included in an illustrative formulation of an inventive composition described in the Examples. A cyclo dextrin is optionally included in an inventive composition in the range 0.1-90% by weight, preferably 0.35-55.0% by weight, based on the total weight of the composition.

In a further embodiment propylene glycol is optionally included in an inventive composition as a carrier. In addition, a combination of propylene glycol and a cyclodextrin may be included.

Further details of carriers having advantages in topical formulations are known in the art and may be found in such standard references as Remington's Pharmaceutical Sciences by Joseph P. Remington, Mack Pub. Co., 1985 and A. Gennaro, Remington: The Science and Practice of Pharmacy, 2000, Lippincott, Williams & Wilkins. Further information may be found in Chang, R., Shojaei, A. Effect of Hydroxypropyl beta-Cyclodextrin on drug solubility in water-propylene glycol mixtures, 2004, Drug Development Indust. Pharmacy 30:297-302; and Francois, M., Snoeckx, E, Putteman, P., Wouters, F., De Proost, E., Delaet, U. Peeters, J., and Brewster, M. A Mucoadhesive Cyclodextrin-based vaginal cream formulation of Itraconazole, 2003, AAPS Pharm.Sci. 5:1-5.

Process For Inhibiting Growth of a Cell

A process of inhibiting a viral infection is provided according to the present invention which includes providing a pharmaceutical composition as described herein and contacting a cell infected with a human papilloma virus with an amount of the composition effective to inhibit growth of the cell.

In one embodiment, a process of inhibiting a viral infection is provided according to the present invention which includes providing a pharmaceutical composition as described herein and contacting a plurality of cells with the composition, wherein a first population of the plurality is infected with a human papilloma virus and a second population of the cells are uninfected and selectively inhibiting growth of the first population of cells infected with the virus without toxic effect on the second population of cells uninfected by the virus.

In a further embodiment, a process of inhibiting a viral infection is provided according to the present invention which includes providing a pharmaceutical composition as described herein and contacting a cell infected with a human papilloma virus with an amount of the composition effective to decrease high risk strain HPV DNA, inhibiting viral infection by the high risk HPV.

In a particularly preferred embodiment, the human papilloma virus is a strain of human papilloma virus associated with a predisposition to transform an infected cell, such as a "high risk" strain of human papilloma virus. Such strains include HPV16, HPV18, HPV31, HPV33, HPV39, HPV45, and HPV56.

Further provided is a process of treating a subject infected with a strain of human papilloma virus which includes providing a composition as described herein and administering a therapeutically effective amount of the composition to the subject.

A therapeutically effective amount of a composition is an amount effective to inhibit a high risk strain HPV infection. In one embodiment, a therapeutically effective amount of a composition is an amount effective to inhibit growth of HPV infected cells. In a further embodiment, a therapeutically effective amount of a composition is an amount effective to decrease high risk HPV DNA in treated cells.

In a particularly preferred embodiment, a provided composition is administered by topical administration. For example, a provided composition is advantageously applied to an area of the subject where infected cells are located and/or adjacent to infected cells. An inventive pharmaceutical composition is preferably topically applied to a tissue associated with human papilloma virus infection such as a vaginal, anal, genital, oral, optic or nasal tissue. Also preferred is administration of an inventive pharmaceutical composition to a tissue associated with undesirable growth of cells infected with a human papilloma virus, such as the cervix.

Inhibition of HPV-Infected Cell Growth

The organotypic raft epithelial culture system has been developed as an in vitro system capable of reproducing the complete viral life cycle (6, 7). This system is used to study the complete life cycle of HPV31b (6, 8-13), and infectious stocks of many high-risk HPV types have been produced using this system (6, 7, 14-16). The ability to reproduce the entire HPV life cycle, and ultimately produce infectious virus, allows for the further study of the differentiation-dependent life cycle of HPV and its role in predisposing cells to malignant transformation.

As described in detail in Examples included herein, a composition including an inhbitor and carrier is applied to a plurality of cells and inhibition of HPV-infected cell growth is observed. In one embodiment, application of the inhibitor AAPFcmk demonstrates a marked specific tissue-thinning effect on raft cultures of HPV infected cells, but not on raft cultures of non-HPV containing keratinocytes. In the organotypic raft culture system, the protease inhibitor, AAPFcmk, specifically and dose-dependently caused a thinning of high risk HPV infected raft tissue. This effect is not due to any general toxicity of the treatment nor is it observed in treatment of non-HPV containing carcinoma cells.

Concomitantly, the amount of HPV genomes in cells is also reduced by treatment with an inventive composition. Reduction of HPV DNA is observed for instance using an inventive composition including the inhibitor AAPFcmk on HPV infected raft cultures. No effect of AAPFcmk treatment on levels of total nuclear protease activity of HPV-infected cells in monolayer culture.

The effects of a composition including an inhibitor and carrier on the growth, morphology and viral genome episomal maintenance of high-risk HPV-infected cells, CIN-612 9E and AWCA cells, in organotypic raft cultures is examined as described in the Examples. The 9E cell line is isolated from a CIN 1 lesion, contains episomal HPV31b, and is capable of completing the entire viral life cycle including infectious virus production, while the AWCA cell line is isolated from an invasive cervical carcinoma and contains integrated HPV18. These cells contain different high-risk HPV types and also recapitulate the in vivo morphology of different stages of cervical cancer. Application of an inventive composition including AAPFcmk results in a pronounced, AAPFcmk dose-dependent growth inhibition, the treated rafts appearing markedly atrophic as compared to rafts treated with a cmk inhibitor (GRcmk) specific for trypsin-like protease activity and those exposed to solvent-only (DMSO) control treatments as illustrated by FIGS. 2A-H and 3 A-H. In many cases, apoptotic-like cells are evident in the growth-inhibited raft cultures. An inhibitor (MG132) specific for the proteasome displayed non-selective toxicity at 5 mM (data not shown).

No general toxicity of an inventive composition is observed. In particular, when HFK raft cultures, which are non-infected with HPV, are treated with AAPFcmk and their morphology compared to HFK rafts treated with GRcmk and/or DMSO no growth inhibitory effects are observed. The same concentrations of AAPFcmk that displayed dramatic effects on HPV-infected raft cultures have no detectable morphological effect on non-HPV containing HFK raft cultures as compared to control treatments, as illustrated by FIGS. 4A-H. In contrast, MG132 at 5 mM is non-selectively toxic to raft cultures irrespective of the presence of HPV (not shown).

Furthermore, the effects of an inventive composition containing AAPFcmk on raft cultures are examined with a non-HPV-containing cervical carcinoma cell line to test whether the growth inhibitory effect is associated with a general cancer phenotype. C33A cells are grown in raft cultures and treated as above. Treatment with an inventive composition does not have any effects on growth or morphology of the C33A raft cultures (data not shown), as is the case with the HFK raft cultures, thus demonstrating that the AAPFcmk effect is associated selectively with the presence of high-risk HPV infection.

TABLE 1

| Treatment | Raft Cell Culture Type | | | |
| --- | --- | --- | --- | --- |
| | CIN-612 9E | AWCA | HFK | C33A |
| | Growth Inhibition (% Control) | | | |
| 0.25% DMSO (Solvent Control) | None | None | None | None |
| 10 micromolar AAPFcmk | ~10% | ~10-20% | None | None |
| 25 micromolar AAPFcmk | ~80% | ~90% | None | None |
| 50 micromolar AAPFcmk | ~90% | ~90-100% | None | None |
| 10 micromolar GRcmk | None | None | None | None |
| 25 micromolar GRcmk | None | None | None | None |

TABLE 1-continued

| | Raft Cell Culture Type | | | |
|---|---|---|---|---|
| Treatment | CIN-612 9E | AWCA | HFK | C33A |
| | Growth Inhibition (% Control) | | | |
| 50 micromolar GRcmk | None | None | None | None |

Table 1 summarizes results of treatment of cells with an inventive composition.

The episomal maintenance of the HPV genome in raft culture with treatment by an inventive composition including AAPFcmk is examined. For this study the CIN-612 9E cell line is used, which exhibits growth inhibition by AAPFcmk in raft cultures (FIGS. 2C-E). Cells are grown and treated as described for the raft culture morphological studies, with varying concentrations of AAPFcmk, GRcmk (specific for trypsin-like activity), or DMSO. A dose-dependent decrease in copy number of HPV31b genomes is observed, with a 75 percent decrease (on a per mg basis) noted with 50 mM AAPFcmk treatment (FIG. 1). Since cell number is reduced by 80-90 percent, this indicates a 95-98 percent decrease in viral DNA following this treatment. In contrast, treatment with GRcmk does not affect HPV31 genome copy number. Thus, AAPFcmk strongly affects the episomal maintenance of HPV31.

An unexpected finding is the identification of a protease inhibitor as a selective inhibitor of the differentiated growth of HPV-infected cells. The effect of an inventive composition including AAPFcmk is examined on HPV infected cells growing in an environment of differentiating tissue that allows for the virus to complete its natural life cycle. In the organotypic raft culture system, AAPFcmk specifically causes a marked growth inhibition with attendant thinning of high-risk HPV infected epithelium, in a dose-dependent manner. This effect is not due to any general toxicity of the treatment, and it is not observed with cervical carcinoma cells not containing HPV, or with uninfected HFK cells.

Without limitation respecting inventive compositions and processes, it is believed that one basis for AAPFcmk induction of growth inhibition may be that the subpopulation of cells most affected by the AAPFcmk treatment is no longer present after the treatments. Further, the effects produced by AAPFcmk may be due to inhibition of the Nuclear Chymotrypsin-like Protease Activity, to inhibition of other chymotrypsin-like proteases, or to actions on proteins other than proteases. In this regard, the AAPF chloromethylketone protease inhibitor, also interacts with ATP-dependent helicases. It is indicated that a helicase activity of the SV40 large T antigen is inhibited in concentration dependent manner by AAPFcmk, and that the growth inhibition produced by the protease inhibitor is dependent upon T Ag having helicase activity, and having it in the nucleus. Alternatively the E1 protein might have chymotrypsin-like activity. Further, aromatic amino acid residues are implicated in helicase activity, see, for instance, Aratani, S., Fujii, R., Fujita, H., Fukamizu, A., and Nakajima, T. Aromatic residues are required for RNA helicase A mediated transactivation. 2003. Int. J. Mol. Med. 12:175-180, which may indicate a mechanism of action of helicase inhibition by a protease inhibitor including an aromatic residue such as AAPFcmk.

Regardless of the biological mechanisms involved, the therapeutic advantages of an inventive composition are immediately apparent. Inventive compositions have growth inhibitory effects that are selective for cells infected with high-risk HPV types. Further, inventive compositions are an important topical therapeutic for the negative selection of HPV-infected cells in the differentiating tissue environment, most importantly cervical dysplasias.

The following examples are included for the purpose of illustrating various embodiments of the invention and are not meant to limit the present invention in any fashion.

EXAMPLES

Example 1

Keratinocyte and Organotypic Raft Cultures

Primary human foreskin keratinocytes (HFKs) are isolated from newborn circumcision as described previously (15). Briefly, the dermis is removed from the epidermis and discarded. The epidermis is washed three times with PBS containing 50 micrograms/milliliter gentamycin sulfate (Gibco-Invitrogen) and 100 U/mL nystatin (Sigma). The epidermis is then minced and trypsinized into a single cell suspension in a spinner flask. HFKs are grown in 154 medium (Cascade Biologics, Inc., Portland, Oreg.) supplemented with Human Keratinocyte Growth Supplement Kit (Cascade Biologics, Inc.). Keratinocyte lines stably maintaining HPV DNA-CIN-612 9E cells containing HPV31b (refs 26, 27), HPV16, HPV18, HPV31 a, HPV33, HPV39, HPV45, NTERT-11, NTERT-31a) and NTERT cells (HPV negative, ref 28) C33a cells (HPV negative, ref 29), and AWCA cells (HPV 18, ref 30) are grown in monolayer culture using E medium in the presence of mitomycin C-treated J2 3T3 feeder cells (6, 7, 31). Monolayer cultures for protease inhibitor assays are grown for 24 hr in 10 mL of E medium supplemented with 50 micromolar of an inhibitor of trypsin-like protease activity GRcmk (Enzyme Systems Products) as a cmk control, 50 micromolar of the protease inhibitor AAPFcmk (Enzyme Systems Products), 5 micromolar MG132 proteasome inhibitor control (Calbiochem, La Jolla, Calif.), or DMSO alone as a solvent control (0.25%). The cultures are treated for either 24 hours, or for 10 days with treatment and media changes every other day. J2 3T3 feeder cells are grown as previously described in DMEM (Gibco-Invitrogen) supplemented with 10% FBS and gentamycin.

Organotypic (raft) cultures are grown as previously described (6, 7, 31). Briefly, cell lines are seeded onto rat tail type 1 collagen matrices containing J2 3T3 feeder cells. Following cell attachment and growth to confluence, the matrices are lifted onto stainless steel grids. Once at the air-liquid interface, the raft cultures are fed by diffusion from below with E medium or with E medium supplemented with either 10, 25, or 50 micromolar GRcmk, 10, 25, or 50 micromolar AAPFcmk, 5 micromolar MG132 proteasome inhibitor, or DMSO alone as a solvent control. Because viral gene expression has been shown to peak between 10 and 12 days in the raft system (13), the raft cultures are allowed to stratify and differentiate for 10 days. Over this growth period, treatments are changed every other day.

Example 2

Southern Blot Hybridization

Total cellular DNA is isolated from CIN-612 9E raft cultures as described previously (6, 12). 5 micrograms of total cellular DNA is digested with either BamHI (an HPV31 non-cutter) or HindIII (an HPV31 single-cutter). The DNA is then separated by 0.8% agarose gel electrophoresis and transferred onto GeneScreen Plus membrane (New England Nuclear Research Products, Boston, Mass.) as described previously (12). Hybridization of the Southern blot is performed as described previously (6, 12), probing with a $^{32}$P-labeled HPV31 specific complete genomic probe.

Example 3

Histochemical Analyses

Raft cultures are grown for 10 days, harvested, fixed in 10% neutral buffered formalin, and embedded in paraffin. 4 micron sections are cut and stained with hematoxylin and eosin as described previously (6). Images are captured at 20× magnification using a Nikon microscope and digital camera.

Example 4

Morphology of HFK, 9E, AWCA, and C33A Raft Cultures

As the life cycle of HPV is tightly linked to the differentiation state of the host tissue and elevated protease activity is correlated with high risk HPV infection, it is deisrable to determine the effect of the AAPFcmk relatively specific NSPA inhibitor on the morphology of CIN-612 9E and AWCA raft cultures. The 9E cell line is isolated from a CIN 1 lesion, contains episomal HPV31b, and is capable of completing the entire viral life cycle including infectious virus production, while the AWCA cell line is isolated from an invasive cervical carcinoma and contains integrated HPV18. These cell lines are chosen as they contain different high risk HPV types and also mimic the in vivo morphology of different stages of cervical cancer.

Examination of raft cultures of these cells demonstrates that AAPFcmk treatment yields a dose-dependent pronounced thinning of both types of raft cultures containing HPV as compared to control treatments.

In order to determine that this effect is not due to a general toxicity of AAPFcmk and is specific to HPV containing raft cultures, HFK raft cultures are treated with AAPFcmk and their morphology compared to HFK rafts treated with a non-specific trypsin inhibitor GRcmk and DMSO as a solvent only control. Such treatment demonstrates that the same concentrations of AAPFcmk having growth inhibiting effects on HPV infected raft cultures have no detectable morphological effect on non-HPV containing HFK rafts as compared to control treatments.

Further examination includes examination of raft cultures of C33A cells which are non-HPV containing carcinoma cells. As is the case with the non-HPV infected HFK raft cultures, AAPFcmk does not affect the tissue morphology of the non-infected C33A raft cultures.

Effects of AAPFcmk, GRcmk, and DMSO on CIN-612 9E Organotypic Raft Cultures.

CIN-612 9E cells, which contain episomal high risk HPV31b, are grown in organotypic raft culture as described. Treatments are made every other day with feeding for 10 days, and the rafts are harvested, fixed, sectioned and stained with hematoxylin and eosin. Rafts are either untreated (FIG. 2A), or treated with 0.25% DMSO solvent control (FIG. 2B), 10 micromolar AAPFcmk (FIG. 2C), 25 micromolar AAPFcmk (FIG. 2D), 50 micromolar AAPFcmk (FIG. 2E), 10 micromolar GRcmk (FIG. 2F), 25 micromolar GRcmk (FIG. 2G), 50 micromolar GRcmk (FIG. 2H), or 5 micromolar MG132 proteasome inhibitor, which prevented the rafts from growing at all (not shown). Of note is the significant raft thinning by the treatments (FIG. 2D and FIG. 2E) of AAPFcmk. Images are taken at 20× magnification.

Effects of AAPF$_{cmk}$, GR$_{cmk}$, and/or DMSO on AWCA Organotypic Raft Cultures.

Figure 3A:
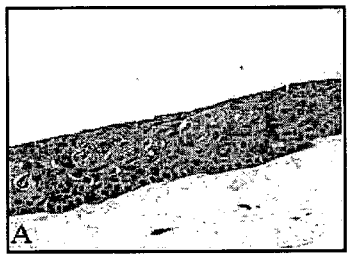
FIG. 3A is a digital image of untreated HPV18 infected AWCA cells grown in organotypic raft culture.
Figure 3B:
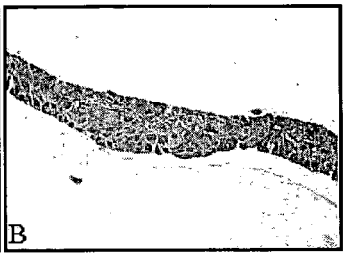
FIG. 3B is a digital image of HPV18 infected AWCA cells grown in organotypic raft culture treated with 0.25% DMSO solvent control.
Figure 3C:
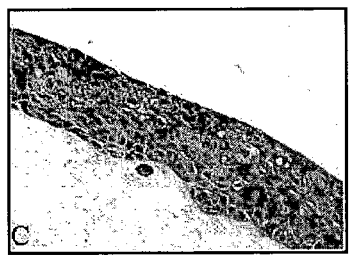
FIG. 3C is a digital image of HPV18 infected AWCA cells grown in organotypic raft culture treated with 10 micromolar AAPFcmk.
Figure 3D:
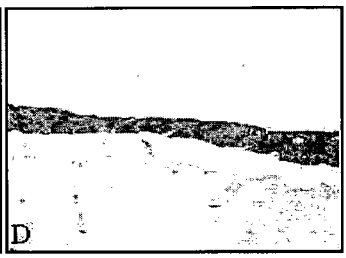
FIG. 3D is a digital image of HPV18 infected AWCA cells grown in organotypic raft culture treated with 25 micromolar AAPFcmk.
Figure 3E:
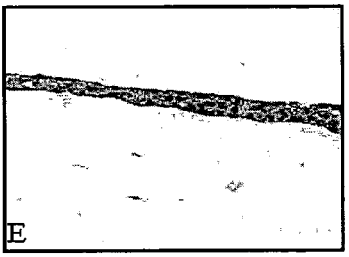
FIG. 3E is a digital image of HPV18 infected AWCA cells grown in organotypic raft culture treated with 50 micromolar AAPFcmk.
Figure 3F:
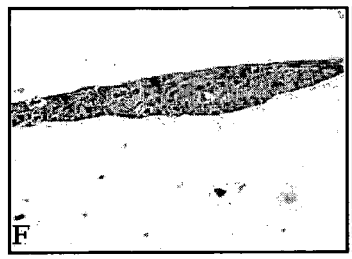
FIG. 3F is a digital image of HPV18 infected AWCA cells grown in organotypic raft culture treated with 10 micromolar GRcmk.
Figure 3G:
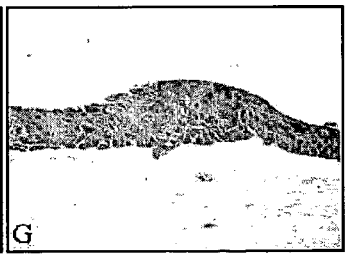
FIG. 3G is a digital image of HPV18 infected AWCA cells grown in organotypic raft culture treated with 25 micromolar GRcmk.
Figure 3H:
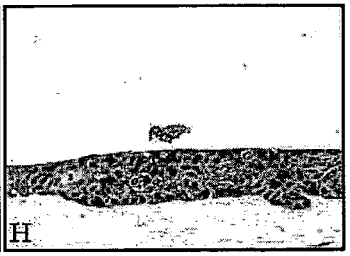
FIG. 3H is a digital image of HPV18 infected AWCA cells grown in organotypic raft culture treated with 50 micromolar GRcmk.

AWCA organotypic raft cultures are treated with AAPFcmk, GRcmk, and DMSO. AWCA cells, which contain integrated HPV18, are grown in organotypic raft culture as described. Treatments are made every other day with feeding for 10 days, and the raft cultures are harvested, fixed, sectioned and stained with hematoxylin and eosin. Rafts are either untreated (FIG. 3A), or treated with 0.25% DMSO solvent control (FIG. 3B), 10 micromolar AAPFcmk (FIG. 3C), 25 micromolar AAPFcmk (FIG. 3D), 50 micromolar AAPFcmk (FIG. 3E), 10 micromolar GRcmk (FIG. 3F), 25 micromolar GRcmk (FIG. 3G), 50 micromolar GRcmk (FIG. 3H). Of note is the significant attenuation of the raft cultures thinning by the treatments (FIG. 3D and FIG. 3E) of AAPFcmk. Images are taken at 20× magnification.

Effects of AAPFcmk, GRcmk, and/or DMSO on HFK Organotypic Raft Cultures.

Figures 4A, 4B:
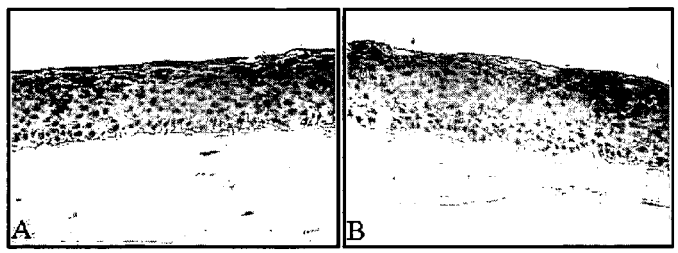
FIG. 4A is a digital image of untreated primary non-HPV infected HFKs grown in organotypic raft culture.
FIG. 4B is a digital image of primary non-HPV infected HFKs grown in organotypic raft culture treated with 0.25% DMSO solvent control.
Figures 4C, 4D, 4E:
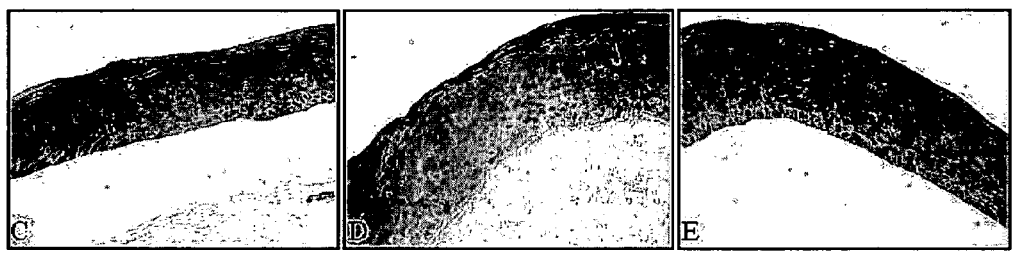
FIG. 4C is a digital image of primary non-HPV infected HFKs grown in organotypic raft culture treated with 10 micromolar AAPFcmk.
FIG. 4D is a digital image of primary non-HPV infected HFKs grown in organotypic raft culture treated with 25 micromolar AAPFcmk.
FIG. 4E is a digital image of primary non-HPV infected HFKs grown in organotypic raft culture treated with 50 micromolar AAPFcmk.
Figures 4F, 4G, 4H:
FIG. 4F is a digital image of primary non-HPV infected HFKs grown in organotypic raft culture treated with 10 micromolar GRcmk.
FIG. 4G is a digital image of primary non-HPV infected HFKs grown in organotypic raft culture treated with 25 micromolar GRcmk.
FIG. 4H is a digital image of primary non-HPV infected HFKs grown in organotypic raft culture treated with 50 micromolar GRcmk.

Primary non-HPV infected HFKs are grown in organotypic raft culture as described. Treatments are made every other day with feeding for 10 days, and the rafts are harvested, fixed, sectioned and stained with hematoxylin and eosin. Rafts are either untreated (FIG. 4A), or treated with 0.25% DMSO solvent control (FIG. 4B), 10 micromolar AAPFcmk (FIG. 4C), 25 micromolar AAPFcmk (FIG. 4D), 50 micromolar AAPFcmk (FIG. 4E), 10 micromolar GRcmk (FIG. 4F), 25 micromolar GRcmk (FIG. 4G), 50 micromolar GRcmk (FIG. 4H). Notable is the lack of the thinning effects in FIG. 4D and FIG. 4E that is observed in HPV containing cells. Images are taken at 20× magnification.

C33A organotypic raft cultures treated with AAPFcmk, GRcmk, and DMSO. C33A cells, which are derived from a non-HPV containing carcinoma, are grown as organotypic raft cultures as described. Treatments are made every other day with feeding for 10 days, and the rafts are harvested, fixed, sectioned and stained with hematoxylin and eosin. Rafts are either untreated, or treated with 0.25% DMSO solvent control, 25 micromolar AAPFcmk, 50 micromolar AAPFcmk, 25 micromolar GRcmk, or 50 micromolar GRcmk. Of note is the lack of effect of AAPFcmk treatment on the raft growth. Images are taken at 20× magnification (not shown).

Example 5

Effects of AAPF$_{cmk}$ on HPV Genome Copy Number in the CIN-612 9E Cell Line.

CIN-612 9E cells are grown in organotypic raft culture as described. Treatments of 0.25% DMSO and AAPFcmk and GRcmk are applied to the raft cultures every other day with feeding over the course of 10 days. DNA is harvested and either digested with a non-cutter of the HPV31 genome, BamHI (B), or a single-cutter, Hind III (H), and a Southern blot performed as described with a $^{32}$P-labelled probe to the HPV31 genome and 100, 10 and 1 copy number per cell controls. A resultant Southern blot is shown in FIG. 1. Form II DNA (nicked supercoiled) and Form I DNA (supercoiled) episomal HPV31 bands are observed in the uncut lanes and Form III DNA (linear) is seen in the single cut lanes. Note the dose-dependent decrease of episomal HPV DNA; it is reduced by ~50% with 25 micromolar AAPFcmk, and by ~75% with 50 micromolar AAPFcmk. Since this is accompanied by an 80-90% decrease in DNA in the AAPFcmk-treated raft cultures, this indicates a 95-98% reduction in viral DNA. This therefore indicates a loss of detectable viral DNA by in situ hybridization.

Example 6

An exemplary formulation of a pharmaceutical composition according to the invention includes a carrier containing cyclodextrin. Preparation of a composition may be accomplished as follows:

Calculation Based on 25 Microliter Treatment Application Volume:

45% Hydroxy-beta-cyclodextrin (HβCD): 2.25 g HβCD is mixed with 3.5 milliliters sterile $H_2O$. Vortex it well then go to 5 milliliters mark with sterile $H_2O$. Store at 4° C. For 45% HβCD treatment, take 1.95 microliters inhibitor at an appropriate concentration and add to 23.05 microliters of 45% HβCD solution to achieve the desired final concentration.

Example 7

An exemplary formulation of a pharmaceutical composition according to the invention includes a carrier containing propylene glycol. Preparation of a composition may be accomplished as follows:

Aqueous propylene glycol solution: Advantageously made fresh every time use since the propylene glycol loses activity in $H_2O$ after 24 hr.

Mix the inhibitor and carrier in the same way as 45% HβCD treatment described in Example 6.

Example 8

An exemplary formulation of a pharmaceutical composition according to the invention includes a carrier containing a combination of cyclodextrin and propylene glycol as a carrier. Preparation of a composition may be accomplished as follows:

Combination of HβCD and Propylene Glycol:

Mix 1.95 microliters of an inhibitor at an appropriate concentration in 2.5 microliters of 10% aqueous propylene glycol or 1.25 microliters of 5% aqueous propylene glycol by vortexing then add the mixture to an appropriate amount of HβCD (55%) stock solution so the total volume is 25 microliters.

Example 9

Inhibitor Penetration in Cervical Tissue

Penetration of an inhibitor included in an inventive composition is examined in an ex-vivo human tissue.

1) Fresh healthy cervical tissue punches measuring 10 millimeters in diameter are obtained from women undergoing hysterectomy. Tissue is obtained from the cervicalmucosa around the "transition zone", which is the junction between mucosal surfaces where cervical cancers arise.

2) The cervical tissue punch is prepared by trimming 1-2 millimeters from the mucosal layer in the connective tissue.

3) The tissue sample is placed in between the receiver and donor compartments of a Franz Diffusion Chamber and it is clamped into place.

4) Receiver compartment is filled with phosphate buffer saline (PBS, pH 7.4) and the temperature is controlled at 37° C.

5) Donor compartment is filled with 25 micrograms of inhibitor (~5 micrograms of labeled inhibitor and ~20 micrograms of unlabeled inhibitor) in 25 microliters of different carriers (i.e. 0, 5, 10, 25, 50% Propylene glycol (PG), or 0, 22.5, 45% hydroxypropyl β cyclodextrin (HβCD), or a combination of both in water). A label is a radioactive label such as $^3H$, a fluorescent label such as fluorescein and/or an affinity reaction label such as biotin.

6) After application, wells are covered with parafilm to prevent evaporation.

7) At 24 hrs, the donor solution is removed and washed with 0.2 milliliters PBS (3×). These are all pooled and prepared for detection. For instance, where the label is radioactive, the sample is added to 10 ml Ecolite scintillation liquid. Also, collect the solution from the receiver compartment. The radioactivity from donor and receiver compartments are corrected into inhibitor concentration values.

8) At 24 hrs, tissue is removed and washed once with water then it is cut into halves: half fixed whole in neutral buffer formaline (10% NBF) for subsequent histology and label detection such as optical detection or half is sliced off mucosa and tissue for label quantification, such as by scintillation counting.

Penetration by the inhibitor of up to 80% of the thickness of the mucosal layer is likely.

REFERENCES

1. A. Mohar, M. Frias-Mendivil, Cancer Invest 18, 584 (2000).
2. H. zur Hausen, Virology 184, 9 (Sep. 1991).
3. H. zur Hausen, Cancer Res 49, 4677 (Sep. 1, 1989).
4. E. I. Grussendorf, H. zur Hausen, Arch Dermatol Res 264,55 (Feb. 23, 1979).
5. P. M. Howley, in Fields Virology B. N. Fields, D. M. Knipe, P. M. Howley, Eds. (Lippincott-Raven Publishers, Philadelphia, 1996) pp. 2045-2070.
6. C. Meyers, M. G. Frattini, J. B. Hudson, L. A. Laimins, Science 257, 971 (1992).
7. C. Meyers, T. J. Mayer, M. A. Ozbun, J Virol 71, 7381 (1997).
8. M. G. Frattini, H. B. Lim, L. A. Laimins, Proc Natl Acad Sci USA 93, 3062 (1996).
9. M. A. Ozbun, C. Meyers, J Virol 73, 3505 (1999).
10. M. A. Ozbun, C. Meyers, in Current Topics in Virology. (1999), vol. 1, pp. 203-217.
11. M. A. Ozbun, C. Meyers, J Virol 72, 2715 (1998).
12. M. A. Ozbun, C. Meyers, Virology 248, 218 (Sep. 1, 1998).
13. M. A. Ozbun, C. Meyers, J Virol 71, 5161 (1997).
14. C. Meyers et al., J Virol 76, 4723 (May, 2002).
15. M. E. McLaughlin-Drubin, S. Wilson, B. Mullikin, J. Suzich, C. Meyers, Virology 312, 1 (Jul. 20, 2003).
16. M. E. McLaughlin-Drubin, N. D. Christensen, C. Meyers, Virology 322, 213 (May 1, 2004).
17. A. R. Kennedy, Pharmacol Ther 78, 167 (1998).
18. U. Wintersberger, Adv Enzyme Regul 22, 311 (1984).
19. R. d'Ari, Biochimie 67, 343 (1985).
20. E. M. Witkin, Bacteriol Rev 40, 869 (Dec. 1976).
21. G. C. Walker, Annu Rev Biochem 54, 425 (1985).
22. M. Radman, in Molecular Mechanisms for the Repair of DNA P. Hanawalt, R. B. Setlow, Eds. (Plenum, N.Y. 1975) pp. 355-367.
23. Z. A. Tokes, G. A. Clawson, J Biol Chem 264, 15059 (1989).
24. D. A. Drubin, G. A. Clawson, Cancer Letters 213, 39 (2004).
25. G. A. Clawson, L. Ren, H. C. Isom, Hepatology 22, 1230 (1995).
26. G. A. Clawson, L. L. Norbeck, J. P. Wise, S. R. Patierno, Cell Growth Differ 4, 589 (1993).

27. M. E. McLaughlin-Drubin, C. Meyers, Virology 321, 173 (Apr. 10, 2004).

28. M. A. Dickson et al., Mol Cell Biol 20, 1436 (Feb. 2000).

29. S. Duensing, K. Munger, Int J Cancer 109, 157 (Mar. 20, 2004).

30. H. Stoppler, M. C. Stoppler, A. Adduci, D. Koval, R. Schlegel, Virology 217, 542 (Mar. 15, 1996).

31. Fields, B. N. 1996. Virology, Third ed. Lippincott-Raven Publishers, Philadelphia-N.Y.

32. Bosch, F. X., and N. Munoz. 2002. The viral etiology of cervical cancer. Virus Res 89:183-90.

33. 1995 IARC Monographs on the evaluation of carcinogenic risks to humans, Human Papillomaviruses, vol. 64. International Agency for Research on Cancer/World Health Organization, Lyon (France).

34. Woodworth, C. D., J. Doniger, and J. A. DiPaolo. 1989. Immortalization of human foreskin keratinocytes by various human papillomavirus DNAs corresponds to their association with cervical carcinoma. J Virol 63:159-64.

35. Durst, M., D. Glitz, A. Schneider, and H. zur Hausen. 1992. Human papillomavirus type 16 (HPV 16) gene expression and DNA replication in cervical neoplasia: analysis by in situ hybridization. Virology 189:132-40.

36. Lancaster, W. D., C. Castellano, C. Santos, G. Delgado, R. J. Kurman, and A. B. Jenson. 1986. Human papillomavirus deoxyribonucleic acid in cervical carcinoma from primary and metastatic sites. Am J Obstet Gynecol 154:115-9.

37. Schwarz, E., U. K. Freese, L. Gissmann, W. Mayer, B. Roggenbuck, A. Stremlau, and H. zur Hausen. 1985. Structure and transcription of human papillomavirus sequences in cervical carcinoma cells. Nature 314:111-4.

38. Stoler, M. H., C. R. Rhodes, A. Whitbeck, S. M. Wolinsky, L. T. Chow, and T. R. Broker. 1992. Human papillomavirus type 16 and 18 gene expression in cervical neoplasias. Hum Pathol 23:117-28.

Any patents or publications mentioned in this specification are herein incorporated by reference to the same extent as if each individual publication is specifically and individually indicated to be incorporated by reference. In particular, U.S. Provisional Patent Application 60/552,026 filed Mar. 10, 2004, is incorporated herein by reference in its entirety.

One skilled in the art will readily appreciate that the present invention is well adapted to carry out the objects and obtain the ends and advantages mentioned, as well as those inherent therein. The compositions and processes described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

We claim:

1. A process of inhibiting a viral infection, comprising:
providing a composition comprising:
a peptide halomethyl ketone inhibitor of a chymotrypsin or chymotrypsin-like protease, and a pharmaceutically acceptable carrier; and
contacting a cell infected with a human papilloma virus with an amount of the composition effective to inhibit growth of the cell, such that a viral infection is inhibited.

2. The process of claim 1 wherein the human papilloma virus is a strain of human papilloma virus associated with a predisposition to transform an infected cell.

3. The process of claim 1 wherein the human papilloma virus is selected from the group consisting of: HPV16, HPV18, HPV31, HPV33, HPV39, HPV45, and HPV56.

4. A process of treating a subject infected with a strain of human papilloma virus, comprising:
providing a composition comprising:
a peptide halomethyl ketone inhibitor of a chymotrypsin or chymotrypsin-like protease, and a pharmaceutically acceptable carrier; and
administering a therapeutically effective amount of the composition to the subject infected with a strain of human papilloma virus.

5. The process of claim 4 wherein the strain of human papilloma virus is a strain associated with a predisposition to transform an infected cell.

6. The process of claim 4 wherein the human papilloma virus is selected from the group consisting of: HPV16, HPV18, HPV31, HPV33, HPV39, HPV45, and HPV56.

7. The process of claim 4 wherein the step of administering includes topical administration.

8. A process of inhibiting a viral infection, comprising:
providing a composition comprising:
a peptide halomethyl ketone inhibitor of a chymotrypsin or chymotrypsin-like protease, and a pharmaceutically acceptable carrier; and
contacting a cell infected with a human papilloma virus with an amount of the composition effective to decrease viral DNA in the cell, such that a viral infection is inhibited.

9. The process of claim 8 wherein the human papilloma virus is a strain of human papilloma virus associated with a predisposition to transform an infected cell.

10. The process of claim 8 wherein the human papilloma virus is selected from the group consisting of: HPV16, HPV18, HPV31, HPV33, HPV39, HPV45, and HPV56.

11. A process of inhibiting a viral infection, comprising:
providing a composition comprising:
a peptide halomethyl ketone inhibitor of a chymotrypsin or chymotrypsin-like protease, and a pharmaceutically acceptable carrier; and
contacting a plurality of cells with a therapeutic amount of the composition, the plurality of cells comprising a first population of cells infected with a human papilloma virus and a second population of cells uninfected by the human papilloma, the therapeutic amount of the composition effective to selectively inhibit growth of the first population of cells and non-toxic to the second population of cell, such that a viral infection is inhibited.

12. The process of claim 11 wherein the human papilloma virus is a strain of human papilloma virus associated with a predisposition to transform an infected cell.

13. The process of claim 11 wherein the human papilloma virus is selected from the group consisting of: HPV16, HPV18, HPV31, HPV33, HPV39, HPV45, and HPV56.

* * * * *

UNITED STATES PATENT AND TRADEMARK OFFICE
CERTIFICATE OF CORRECTION

PATENT NO.         : 7,402,561 B2
APPLICATION NO.    : 11/076680
DATED              : July 22, 2008
INVENTOR(S)        : Gary Clawson et al.

It is certified that error appears in the above-identified patent and that said Letters Patent is hereby corrected as shown below:

Title Pg, Item (56) "OTHER PUBLICATIONS" delete "Stoppler, et al., Oncogene, 1996, 13, 1545-1548*"

Column 17, line 11, replace "go" with --qs--

Signed and Sealed this

Eleventh Day of November, 2008

JON W. DUDAS
*Director of the United States Patent and Trademark Office*